United States Patent [19]

Barben et al.

[11] Patent Number: 5,465,578
[45] Date of Patent: Nov. 14, 1995

[54] THERMOELECTRIC GAS SAMPLE COOLER

[75] Inventors: Ted Barben; Randy Carlson; Kurt Christner; Heinz Doring, all of Carson City, Nev.

[73] Assignee: Universal Analyzers, Inc., Carson City, Nev.

[21] Appl. No.: 183,328

[22] Filed: Jan. 19, 1994

[51] Int. Cl.⁶ ............................. F25B 21/02; F25D 17/06
[52] U.S. Cl. .................. 62/3.2; 62/3.7; 136/203; 29/890.03
[58] Field of Search ................... 62/3.2, 3.7, 3.4; 136/203; 29/890.03

[56] References Cited

U.S. PATENT DOCUMENTS

| | | | |
|---|---|---|---|
| Re. 31,333 | 8/1983 | Barben, II | 324/450 |
| 4,182,129 | 1/1980 | Haunold et al. | 62/3.2 |
| 4,487,619 | 12/1984 | Jones | 62/3.7 |
| 4,494,380 | 1/1985 | Cross | 62/3.2 |
| 4,745,759 | 5/1988 | Bauer et al. | 62/3.2 |
| 5,042,257 | 8/1991 | Kendrick et al. | 62/3.1 |
| 5,095,973 | 3/1992 | Toy | 165/185 |
| 5,147,524 | 9/1992 | Broadley | 204/433 |
| 5,269,146 | 12/1993 | Kerner | 62/3.6 |
| 5,279,128 | 1/1994 | Tomatsu et al. | 62/3.4 |

FOREIGN PATENT DOCUMENTS

| | | | |
|---|---|---|---|
| 4036210 | 5/1992 | Germany | 62/3.7 |
| 3083521 | 4/1988 | Japan | 62/3.2 |

*Primary Examiner*—Henry A. Bennet
*Assistant Examiner*—William C. Doerrler
*Attorney, Agent, or Firm*—Thorpe, North & Western

[57] ABSTRACT

A thermoelectric cooler for cooling a sample of hot, continuously flowing gas involves a mechanical heat flow path passing from the flowing gas through a heat-exchanging tube channeling the gas, a heat-conductive block housing the tube, a thermoelectric element having a cold side abutting the block, a heat sink abutting a hot side of the thermoelectric element, and cooling air streams passing through slots in the heat sink. The heat sink is a unibody, jointless metallic body having relatively thin fins defining the slots. A high pressure blower drives turbulent air streams through the slots of the heat sink, and a thermal switch is disposed on the heat sink near the hot side of the thermoelectric element.

14 Claims, 1 Drawing Sheet

THERMOELECTRIC GAS SAMPLE COOLER

BACKGROUND OF THE INVENTION

1. The Field of the Invention

The present invention relates generally to thermoelectric gas sample coolers. More particularly, it concerns a temperature controlled, thermoelectric gas sample cooler having a low mass, high-heat-flux unibody heat sink cooled by high-pressure turbulent air streams.

2. The Background Art

Incinerators, smoke stacks and other industrial equipment are known to emit large quantities of hot, vaporous gases into the atmosphere. In the interest of environmental protection and plant efficiency, such industrial gaseous emissions are frequently analyzed and evaluated as to compliance with governmental and in-house specifications. These gaseous emissions can be more effectively analyzed if the gas sample is transformed into a dry and cooled state. Of current interest are apparatus for quickly and efficiently removing heat from hot, gaseous emissions to thereby cool the gas to a predetermined temperature suitable for analysis.

Thermoelectric gas sample coolers are known in the art for cooling hot gas samples. These prior art coolers include a heat-exchanging tube through which a sample of hot, continuously-flowing gas is pumped. The heat-exchanging tube is thermoelectrically cooled and maintained at a predetermined temperature such that heat is removed from the gas as it flows through the tube. The heat is mechanically transferred to an air-cooled, metallic heat sink block by a thermoelectric element as known in the art. The heat sink block is large enough to absorb and release heat at a rate sufficient to enable the system to cool the gas along a substantial temperature range, for example from about 200° C. to about 5° C. The gas is gradually cooled as it flows through the tube such that it reaches the desired temperature just prior to discharge.

These prior art thermoelectric coolers are characterized by many disadvantages. The heat sink blocks are quite large, expensive, heavy and bulky due to the following structural particulars. Heat sink blocks comprise a plurality of metallic fins which are glued into a metallic support body to form a plurality of air-flow slots. The fins provide a substantial amount of surface area for contact with the cooling air to thereby accelerate heat removal from the heat sink. Although heat conductive glues can be used to glue in the fins, the glue is somewhat of a barrier against heat flow within the heat sink because the material properties of the glue are not entirely consistent with the metal from which the support body and fins are made. The obstruction to heat flow brought about by the glue requires the heat sink to be larger in order to absorb heat at a rate sufficient to maintain the thermoelectric element and the heat exchanging tube at desired temperatures.

Efforts to reduce the size of the prior art heat sink blocks are also limited by the thickness of the fins. If the fins can be made thinner, then the required amount of fin surface area can be achieved in a smaller heat sink block. However, if a smaller, more efficient heat sink is accomplished, the threat of overheating the thermoelectric element increases because a failure of the cooling air source would result in more heat "back-up."

The prior art gas sample coolers have traditionally been cooled with the use of "muffin fans" as are known in the art for moving large amounts of air at low pressures. The prior art teaches the use of "muffin fans" to suck air through the heat sink slots at low pressure to produce air streams characterized by laminar flow. Laminar air streams are cooler than turbulent air streams because mechanical mixing of the air raises the temperature of the air stream. The conventional wisdom of those skilled in the art teaches that the cooler, laminar air streams will be more effective in cooling the heat sink. Even if there were a prior art practice of applying nonlaminar, turbulent air streams, the fans used in the prior art cannot produce air flow at a pressure high enough to create turbulent air streams within the slots of the heat sink.

There is thus a need to achieve a gas sample cooler having a smaller, more efficient heat sink. There is a further need to provide a cooling apparatus small enough for use in conjunction with a smaller heat sink but capable of moving air at a pressure high enough to produce turbulent air streams within the slots of the heat sink. There is also a need to safeguard against the threat of overheating the thermoelectric element, a threat which is increased by a smaller, more efficient heat sink. Those having ordinary skill in the art will appreciate that these and other needs are met by aspects of the present invention.

OBJECTS AND SUMMARY OF THE INVENTION

It is therefore an object of the present invention to provide a thermoelectric gas sample cooler for cooling a sample of hot, continuously flowing gas to a predetermined temperature.

It is an additional object of the invention to provide such a cooler which is compact and economical.

It is another object of the invention, in accordance with one aspect thereof, to provide such a cooler for producing a more efficient heat transfer.

It is also an object of the invention, in accordance with one aspect thereof, to provide such a cooler for producing cooling air at a relatively high pressure.

It is a further object of the invention, in accordance with one aspect thereof, to provide such a cooler for producing a relatively high degree of cooling air turbulence within the cooler to more effectively cool the heat sink.

It is still another object of the invention, in accordance with one aspect thereof, to provide such a cooler for responding more directly to the temperature of thermoelectric elements within the cooler to thereby prevent overheating thereof.

While the present invention is described in terms of a cooler for cooling a sample of flowing gas, it is to be understood that the principles of the invention may be used in any setting requiring the cooling of a fluidic substance. Those having ordinary skill in the field of this invention will appreciate the advantages of the invention, and its application to a wide variety of uses.

The above objects and others not specifically recited are realized in an illustrative embodiment of a thermoelectric gas sample cooler. The cooler includes heat-exchanging tube for receiving the gas which is housed within a heat-conductive chilled block. A thermoelectric heat-transferring element having opposing hot and cold sides is positioned such that the cold side abuts the chilled block, so that the cold side chills the block, which chills the tube, which cools the gas. A small, unibody heat sink having relatively thin fins extending outward from a support body is positioned against the hot side of the thermoelectric element for absorbing heat therefrom. An open-scroll, rotational drum blower produces turbulent air flow between the fins to thereby cool the heat sink such that the hot side of the thermoelectric element is maintained at a predetermined temperature. A thermal switch is disposed on the heat sink and electrically connected to the thermoelectric element for deactivating said thermoelectric element if the temperature of the heat sink reaches a predetermined threshold value, to thereby prevent overheating of the thermoelectric element.

Additional objects and advantages of the invention will be set forth in the description which follows, and in part will be apparent from the description, or may be learned by the practice of the invention. The objects and advantages of the invention may be realized and obtained by means of the instruments and combinations particularly pointed out in the appended claims.

BRIEF DESCRIPTION OF THE DRAWINGS

The above and other objects, features and advantages of the invention will become apparent from a consideration of the subsequent detailed description presented in connection with the accompanying drawings in which.

Figure 1:
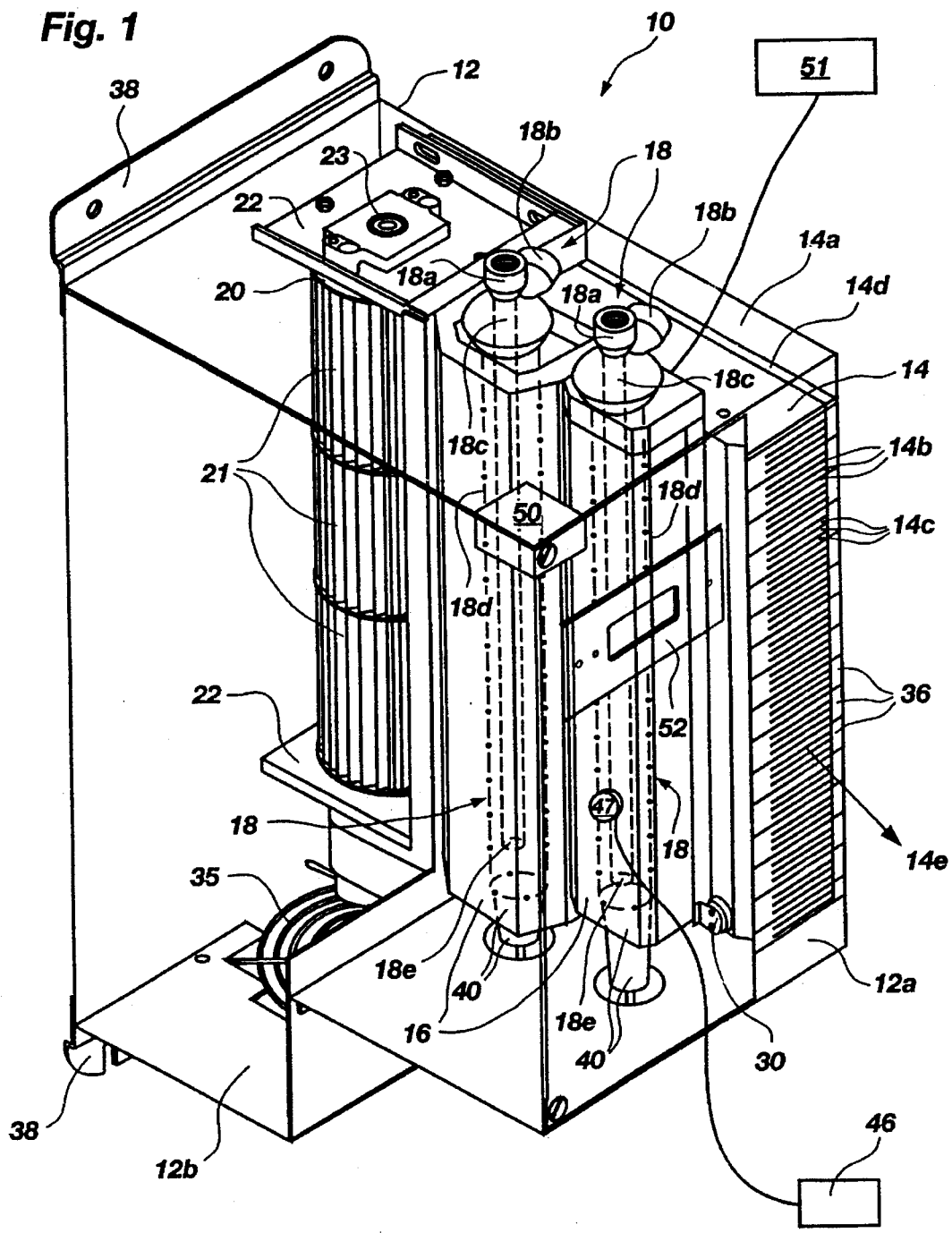
FIG. 1 illustrates a perspective view of a thermoelectric gas sample cooler showing interior components made in accordance with the principles of the present invention.

DETAILED DESCRIPTION OF THE PRESENTLY PREFERRED EXEMPLARY EMBODIMENTS OF THE PRESENT INVENTION

Reference will now be made to the drawings wherein like structures will be provided with like reference numerals.

In FIG. 1 is shown a thermoelectric gas sample cooler, generally designated at 10, for cooling a sample of hot, continuously flowing gas to a predetermined temperature. The cooler 10 includes a vented housing 12 containing a conductive heat sink 14 and two chilled blocks 16. The heat sink 14 comprises a continuous metal and includes a plurality of thin, parallel fins 14b integrally connected to a support plate 14a in a unibody construction. The fins 14b extend outward from the support plate 14a to define a corresponding plurality of air flow slots 14c. A foam elastomeric sheet 14d is disposed against free ends of the slots 14c as shown in FIG. 1 to thereby channel air therein and maintain airflow within said slots substantially in a direction 14e. Any suitable material other than foam may be used for the sheet 14d.

Figure 2:
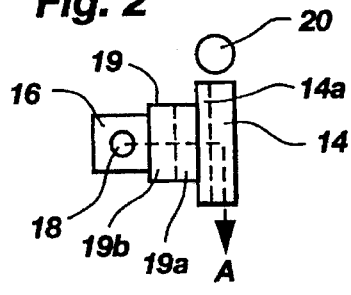
FIG. 2 illustrates a plan, schematic view of a top end portion of the cooler of FIG. 1.

Referring to the schematic representation in FIG. 2, thermoelectric elements 19 (not shown in FIG. 1) as known generally in the art are disposed between the chilled blocks 16 and the heat sink 14. Hot sides 19a of the thermoelectric elements 19 abut the support plate 14a of the heat sink, and opposing cold sides 19b abut the chilled blocks 16. The elongate, chilled blocks 16 each include an axially extending passage for housing a heat-exchanging tube 18 having gas inlet- and gas discharge-nozzles 18a and 18b, respectively. The tube 18 includes an inner tube 18c connected to the inlet nozzle 18a, and a concentric, outer tube 18d in communication with discharge nozzle 18b. The inner and outer tubes 18c and 18d communicate via an open end 18e of inner tube 18c which is open within outer tube 18d at a lower end thereof, as shown in phantom line in FIG. 1.

An open-scroll, rotational drum blower 20 having stages of blades 21 is close coupled to one end of the air flow slots 14c. The term "close coupled," as used herein, refers to the placement of the blower 20 as close as operationally possible to the air flow slots 14c. The blower 20 is rotatably mounted upon mounting blocks 22 with rotational mounting structure 23. A mechanical thermal switch 30 as known in the art is mounted on the support plate 14a near the hot side 19a of the thermoelectric element 19.

Referring to FIG. 1, the housing 12 includes air inlet vents 35 formed in a bottom wall 12b for receiving air, and air discharge vents 36 formed in a front portion 12a for discharging air. The inlet and discharge vents 35 and 36 are positioned such that the flow of inlet and discharge air defines a substantially right angle. Air inlet vents can also be placed in side walls of the housing 12. The housing 12 further includes wall-mounting structure 38. The cooler 10 is thereby mountable against a wall such that air is discharged from the discharge vents 36 in a direction substantially normal to the mounting wall.

Moisture removers 40 are disposed on the bottom of the chilled blocks 16 and are placed in fluid communication with the heat-exchanging tubes 18. These moisture removers 40 may comprise any of a number of available moisture removing aids, for example a peristaltic pump, an eductor, or a water trap using the force of gravity. An alarm 46 is electrically connected to a temperature sensor 47 disposed on one of the chilled blocks 16. A computer controller 52 as known in the art includes the usual circuit boards and appurtenant electronics and is disposed on the front portion 12a of the housing 12. A power source 50 powers the controller 52.

The purpose and interrelationship of the elements identified above will be discussed in more detail below in reference to FIGS. 1–2.

The cooler 10 operates to maintain the heat-exchanging tubes at a predetermined temperature, for example 5° C. This is accomplished in the following manner. The thermoelectric element 19 is electrically powered and operates to maintain the cold side 19b thereof at a predetermined, preset temperature. This is accomplished as known in the field of thermodynamics by the thermoelectric element 19 transferring heat from its cold side 19b to its hot side 19a by means of the electric power supplied to it. The temperature of the cold side 19b is responsive to variation in the temperature of the hot side 19a such that any increase or decrease in the temperature of said hot side 19a brings about a corresponding, substantially equal increase or decrease in the temperature of said cold side 19b. Heat is continually removed from the hot side 19a of the thermoelectric element 19 by the heat sink 14 in order to maintain the temperature of the cold side at a desired level. If heat is not removed fast enough from the hot side, the hot and cold sides will get too hot and cause the solder in the thermoelectric element 19 to melt and the element 19 to overheat.

During use of the cooler 10, the thermoelectric elements 19 operate to establish a mechanical heat flow path as shown schematically in FIG. 2 by arrow A. The gas inlet nozzles 18a are fluidly connected to a gas pump (not shown) which pumps a sample of a hot, continuously flowing gaseous emission therein. The gas flows through the heat-exchanging tubes 18 and is discharged from the gas discharge nozzles 18b. The gas discharge nozzles 18b can be fluidly connected to anything desired by the user, such as a holding tank, a gas sample analyzer, and so forth.

Figure 3:
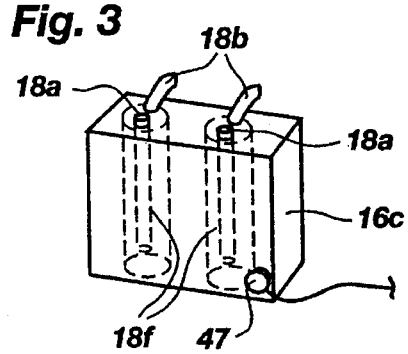
FIG. 3 illustrates a perspective view of an alternative embodiment of a heat conductive block portion of the cooler of FIG. 1.

The heat-exchanging tubes 18 extend into the chilled blocks 16 as shown in phantom in FIG. 1 and comprise elongate, concentric, heat-conductive tubes. A portion of the tubes 18 may comprise a wide, thin duct approximately 1/16 of an inch thick. In the alternative, the tubes 18 can be fluidly separated from their respective discharge nozzles 18b by such a duct formed within the chilled blocks 16. Further, instead of using heat-exchanging tubes 18 and blocks 16, two gas flow passages 18f could be formed in a single, heat-conductive block 16c, as in FIG. 3. There are thus many different combinations possible to define a gas flow path 18f with heat conductive structure.

As the hot gas flows through the heat-exchanging tube 18, it is gradually cooled to a predetermined temperature in the following manner. The cold side 19b of the thermoelectric element 19 is maintained at a temperature sufficient to mechanically chill the block 16, which in turn maintains the heat-exchanging tube 18 at a temperature sufficient to cool the gas flowing therethrough to a predetermined temperature, for example 5° C. In effect, the heat-exchanging tube 18 cools the gas by mechanically removing heat from it. This heat is in turn mechanically removed from the tube 18 by the chilled block 16. The cold side 19b of the thermoelectric element 19 mechanically removes the heat from the chilled block 16, then the heat is removed from the cold side 19b to the hot side 19a. Finally, the heat sink 14 removes the heat from the hot side 19b, and the blower 20 blows ambient air through the heat sink 14 to cool it. The temperature maintained in the heat sink 14 is therefore a function of the ambient air temperature. The ability to maintain the cold side 19b of the element 19 at a certain temperature is thus a function of the size of the heat sink 14, the air pressure from the blower 20, and the ambient air temperature.

The temperature differential between the hot side 19a and the cold side 19b of the thermoelectric element 19 is such that the tube 18, block 16 and cold side 19b remain very cold, and the hot side 19a and the heat sink 14 remain very hot. The blower 20 blows air through the slots 14c of the heat sink 14 to thereby blow heat away from said heat sink into the ambient surrounding air. It can therefore be said that heat from the gas travels along the flowpath designated by arrow A in FIG. 2 and is eventually discharged from the air discharge vents 36 of the housing 12.

The cooling of the gas reduces the gas temperature across a substantial temperature range. For example, the cooler 10 can be used to cool a sample of gas from an industrial smoke stack from 200° C. to 5° C. The resulting temperature extremes experienced by the gas cause vapor therein to condense into a liquid state. The peristaltic pumps 40 are fluidly connected to the heat-exchanging tubes 18 and operate as known in the art to remove the condensed vapor from said tubes 18 without contaminating or otherwise introducing outside gases or other fluids into the flowing gas sample. The sample is thus discharged from the discharge nozzles 18b in a substantially dry, cooled state suitable for analysis.

The temperature sensor 47 monitors the temperature of one of the chilled blocks 16 to insure that the gas sample is sufficiently cooled for the purposes of the user. For example, the user may desire to maintain the gas discharge temperature between about 5° C. and 10° C. The sensor 47 can be set to activate the alarm 46 if the temperature of the chilled block 16 exceeds 10° C., which can occur for example upon failure of the blower 20. The alarm 46 may produce an audible or visual signal to alert the user to deactivate the gas pump and thereby halt the flow of gas through the tubes 18. One temperature sensor 47 is normally sufficient although each chilled block 16 can have its own temperature sensor.

An important aspect of the present invention is the manufacture and use of the heat sink 14. The slots 14c are cut into a body of conductive metal with a saw to produce a unibody heat sink 14. This method produces a heat sink having fins 14b which are significantly thinner than 0.05 inches; fins 14b which are approximately 0.035 inches thick or less can be produced by this method. The resulting unibody heat sink 14 has no internal barriers to heat flow because it is constructed of the same continuous material throughout without any internal bonds, joints or the like. This results in a more efficient heat sink in that heat can flow more quickly from the support plate 14a into the fins 14b.

The efficiency of the heat sink 14 is not only improved by its seamless, unibody nature, but also by the thinner fins 14b. For example, a given amount of fin surface area for contact with cooling air from the blower 20 permits a given rate of heat flow to pass through the heat sink 14. The thinner fins 14b allow a smaller heat sink 14 for a given amount of fin surface area, thereby reducing the volume of metal required to conduct a given rate of heat flow. Thus, the seamless, jointless nature of the heat sink 14 in combination with the thin fins 14c result in a low-mass, high-heat-flux heat sink 14 which is less expensive to make and easier to handle during manufacture and installation.

Another important aspect of the present invention is the addition of the open-scroll, rotational drum blower 20. The prior art teaches the use of low pressure "muffin" fans and the like for producing substantially laminar air streams within the slots of a heat sink. It is thought in the prior art that cooler air streams are better able to cool surrounding channels. Prior art method therefore seek to avoid mixing the cooling air since mixing raises the cooling air temperature. However, applicant has discovered the surprising result that the boundary conditions of the slots 14c are such that cooling air supplied therethrough under turbulent conditions is more effective in removing heat from the heat sink fins 14b. This occurs even though the temperature of a turbulent air stream passing through a slot 14c is slightly higher than a laminar air stream.

The problem with the prior art coolers is that the fans used cannot produce air flow at a pressure high enough to create turbulent air streams within the slots 14c of the heat sink 14. The open-scroll, rotation drum blower 20 drives air through the slots 14c at much higher pressures and flow rates as compared to the prior art fans. The air pressure produced by the blower 20 is high enough to produce turbulent air flow which cools the heat sink 14 to a lower temperature. This enhanced cooling action further improves the efficiency of the heat transfer operation. Since the cooling air from the blower 20 removes heat faster from the fins 14b, the blower 20 allows for a higher rate of heat flow, which in turn allows the heat sink 14 to have less surface area. In effect, the blower 20 further reduces the size of the heat sink required to remove heat at a given heat flow rate.

A further important aspect of the present invention is the addition of the thermal switch 30 to the support plate 14a. Applicant has discovered that the alarm feature 46, while effective in preventing insufficiently-cooled gas from being discharged, is not always effective in preventing the thermoelectric element 19 from overheating. The heat-transfer efficiency gains provided by the unibody heat sink 14 and the high-pressure blower 20 provide a much faster rate of heat flow as discussed above. The resulting heat flow is so fast that if the ambient air temperature is too high or if the blower 20 fails, the thermoelectric element 19 can overheat and burn up. The heat flow can "back up" fast enough to cause the overheating before the sensor 47 has a chance to activate the alarm 46, since the highly efficient heat sink 14 can have a small mass in comparison to the chilled blocks 16. If the thermoelectric element 19 is not turned off quickly upon the occurrence of a heat overload, its temperature will quickly rise above the melting temperature of the solder therein to cause the overheating. Therefore, a more direct temperature sensing feature is necessary.

The thermal switch 30, when placed on the heat sink 14, provides the needed direct temperature sensing feature. The thermal switch 30 is preferably placed on the support plate 14a, which abuts the hot side 19a of the thermoelectric element 19. This permits the switch 30 to be substantially directly responsive to the temperature of the hot side 19a. The thermal switch 30 is electrically connected to the power connection of the thermoelectric element 19 in order to deactivate it if the support plate 14a reaches a predetermined temperature. This prevents the element 19 from overheating. The switch 30 can be set to the overheat temperature of the thermoelectric element 19 or upon any significant deviation from the system heat flow temperature. It is preferable to set the switch 30 at approximately 80° C.

The heat exchanging tubes 18 are preferably made from stainless steel type 316, or alloy 20. Other heat-conductive materials and combinations thereof can be used, such as PVDF plastic or pyrex glass. The chilled blocks 16 are preferably extruded from aluminum. The thermoelectric element 19 comprises ceramic-type wafers as known in the art, such as Peltier pads and the like. It is preferable to use a thermoelectric element which can maintain the cold side at approximately 5° C. and the hot side at approximately 50° C. A preferred embodiment includes two Peltier pads electrically connected in series for each block 16, powered by a twenty-four volt power source 51. This configuration generates less current than two Peltier pads powered in parallel by a twelve volt power source.

The heat sink 14 is preferably aluminum. The thickness of the slots 14c is preferably within a range of approximately 0.09–0.125 inches. The alarm 46 can be separate as shown in FIG. 1, or incorporated into the computer controller 52.

Those having ordinary skill in the relevant art will appreciate many uses for the cooler 10. The cooler 10 is useful in any high heat energy application requiring a heat sink, especially where it is desirable to use a low-mass, high-heat-flux heat sink in a heat flow path involving a higher-mass chilled block or other heat transfer apparatus.

The present invention represents a significant advance over traditional apparatus and methods of cooling gas samples. It is noted that many of the advantages of the present invention accrue due to the unibody and jointless nature of the heat sink, the discovery of the usefulness of turbulent cooling air streams provided by the open-scroll rotational drum blower, and the direct temperature control of the thermal switch. The problems noted above and others not discussed are overcome to a significant degree by the present invention. Those skilled in the art will appreciate from the preceding disclosure that the objectives stated above are advantageously achieved by the present invention.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A thermoelectric gas sample cooler configured for cooling a sample of hot, continuously flowing gas and providing a blower element which moves cooling air in a turbulent flow path within the cooler, said cooler comprising:

a heat-conductive block including means for
(i) receiving the flowing gas into the block to thereby transfer heat from said gas into said block to thereby cool said gas to approximately a first predetermined temperature, and
(ii) discharging the cooled gas for processing;

a thermoelectric cooling element including a hot side and an opposing cold side, said cold side being positioned against the block for mechanically removing heat therefrom to thereby cool and maintain said block at a predetermined temperature;

a heat-conductive sink having a plurality of slots extending therethrough and being positioned against the hot side of the thermoelectric cooling element for mechanically removing heat therefrom to thereby maintain the cold side at a predetermined temperature; and an open-scroll rotational drum blower positioned adjacent to the slots of the heat sink for driving ambient air through the slots at an air pressure sufficient to produce turbulent cooling air streams within said slots to thereby cool said heat sink and carry heat therefrom away from the cooler at a rate sufficient to permit the heat removing means to cool the gas to said first predetermined temperature.

2. A gas sample cooler as in claim 1 wherein the gas receiving means, heat removing means, and gas discharging means collectively comprise hollow, elongate, heat-exchanging tube means disposed within a passage formed in the heat-conductive block, said tube means defining a gas flow path and including a gas inlet nozzle and a gas discharge nozzle disposed thereon at opposing ends of said path for respectively receiving and discharging the sample of flowing gas such that heat is mechanically removed from the gas by the tube, and from the tube by the block.

3. A gas sample cooler as in claim 1 further comprising:

a wall-mounted, vented housing for containing the heat-exchanging tube, the block, the thermoelectric cooling element, the heat sink, and the blower, said housing including:

an air discharge vent formed in a front portion of the housing for discharging the cooling air from the heat sink slots in a direction substantially normal to the mounting wall; and an air inlet vent formed in a wall of the housing such that the flow of inlet and discharge cooling air defines a substantially right angle.

4. A gas sample cooler as in claim 1 further comprising:

means fluidly connected to the heat-exchanging tube for removing therefrom moisture condensed from the gas.

5. A gas sample cooler as in claim 1 further comprising:

means attached to the block and responsive to the temperature thereof for producing an alarm signal when the temperature of said block reaches a predetermined threshold value indicating a need to deactivate a pump-driven gas source to stop the flow of gas into the heat-exchanging tube to thereby prevent the discharge of gas having a temperature substantially higher than said first predetermined temperature from said tube.

6. A gas sample cooler as in claim 1 wherein the blower is positioned as close as operationally possible to the slots of the heat sink.

7. A thermoelectric gas sample cooler configured for cooling a sample of hot, continuously flowing gas and providing a unibody heat absorbing element for dispersing heat into a plurality of heat flow paths, said cooler comprising:

a heat-conductive block including means for
  (i) receiving the flowing gas,
  (ii) mechanically removing heat from said gas to thereby cool said gas to approximately a first predetermined temperature, and
  (iii) discharging the cooled gas for processing;

a thermoelectric cooling element including a hot side and an opposing cold side, said cold side being positioned against the block for mechanically removing heat therefrom to thereby cool and maintain said block at a predetermined temperature;

a conductive, unibody heat sink including a conductive support plate having first and second opposing sides, and a plurality of conductive heat-sink fins extending outwardly from the first side of the support plate in a substantial parallel orientation, said fins being formed from the same material as the support plate such that the support plate and the fins collectively form the unibody heat sink, said heat-sink fins being separated by saw-cut slots to thereby enable each heat-sink fin to have a thickness which does not exceed 0.05 inches, said saw-cut slots having a thickness within a range of approximately 0.09–0.125 inches; and means for moving ambient air through the slots in the heat sink to thereby produce airstreams within said slots for cooling said heat sink to a predetermined temperature and for carrying heat therefrom away from the cooler.

8. A gas sample cooler as in claim 7 wherein the gas receiving means, heat removing means, and gas discharging means collectively comprise hollow, elongate, heat-exchanging tube means disposed within a passage formed in the heat-conductive block, said tube means defining a gas flow path and including a gas inlet nozzle and a gas discharge nozzle disposed thereon at opposing ends of said path for respectively receiving and discharging the sample of flowing gas such that heat is mechanically removed from the gas by the tube, and from the tube by the block.

9. A gas sample cooler as in claim 7 further comprising:
a wall-mounted, vented housing for containing the heat-exchanging tube, the block, the thermoelectric cooling element, the heat sink, and the air moving means, said housing including:
  an air discharge vent formed in a front portion of the housing for discharging the cooling air from the heat sink slots in a direction substantially normal to the mounting wall; and
  an air inlet vent formed in a wall of the housing such that the flow of inlet and discharge cooling air defines a substantially right angle.

10. A gas sample cooler as in claim 7 further comprising:
means fluidly connected to the heat-exchanging tube for removing therefrom moisture condensed from the gas.

11. A gas sample cooler as in claim 7 further comprising:
means attached to the block and responsive to the temperature thereof for producing an alarm signal when the temperature of said block reaches a predetermined threshold value indicating a need to deactivate a pump-driven gas source to stop the flow of gas into the heat-exchanging tube to thereby prevent the discharge of gas having a temperature substantially higher than said first predetermined temperature from said tube.

12. A gas sample cooler as in claim 7 wherein the fins are positioned in a substantially parallel configuration.

13. A gas sample cooler as in claim 7 wherein the fins terminate in free ends opposite said support plate, said heat sink further including a sheet of material disposed against said free ends to thereby block air flow at said free ends and to channel airflow in a direction substantially parallel to the support plate.

14. A gas sample cooler as defined in claim 7, wherein the means for moving ambient air comprises means for driving ambient air through the saw-cut plurality of slots in the heat sink at air pressures sufficient to produce turbulent cooling air streams within said slots.

* * * * *